United States Patent [19]

Kresse et al.

[11] 4,013,067
[45] Mar. 22, 1977

[54] WARNING APPARATUS FOR INDICATING A THREAT OF IMPENDING SHOCK

[75] Inventors: Heinz Kresse, Erlangen; Helmut Reichenberger, Brand, both of Germany

[73] Assignee: Siemens Aktiengesellschaft, Erlangen, Germany

[22] Filed: May 22, 1975

[21] Appl. No.: 579,801

[30] Foreign Application Priority Data

June 26, 1974 Germany .......................... 2430788

[52] U.S. Cl. ..................... 128/2.05 R; 128/2.05 P; 128/2.05 T; 128/2.05 V; 356/39
[51] Int. Cl.² ............................................. A61B 5/02
[58] Field of Search .......... 128/2 R, 2 A, 2 V, 2 L, 128/2.05 R, 2.05 D, 2.05 M, 2.05 P, 2.05 N, 2.05 F, DIG. 29, 2.05 V, 2.05 T; 356/39, 41; 73/DIG. 11; 340/279

[56] References Cited
UNITED STATES PATENTS

| | | |
|---|---|---|
| 3,704,706 | 12/1972 | Herczfeld et al. .............. 128/2.05 P |
| 3,796,213 | 3/1974 | Stephens ....................... 128/2.05 R |
| 3,814,082 | 6/1974 | Taylor .......................... 128/2.05 R |
| 3,847,483 | 11/1974 | Shaw et al. ......................... 128/2 L |
| 3,910,701 | 10/1975 | Henderson et al. ................ 356/39 |

*Primary Examiner*—Richard C. Pinkham
*Assistant Examiner*—Vance Y. Hum
*Attorney, Agent, or Firm*—Haseltine, Lake & Waters

[57] ABSTRACT

A warning apparatus for indicating the threat of impending shock, which includes a photoelectric pulse pickup or receiver adapted to be applied onto the skin of a patient. The pulse pickup or receiver is a combined reflective and transmissive receiver, and the pulse pickup has a signal comparison arrangement associated therewith which compares the signal obtained from a reflective and transmissive measurement with predetermined signal threshold or boundary values, and which will generate an output signal for initiation of an alarm when the output signal of the pulse pickup exceeds the boundary value imparted thereto.

8 Claims, 1 Drawing Figure

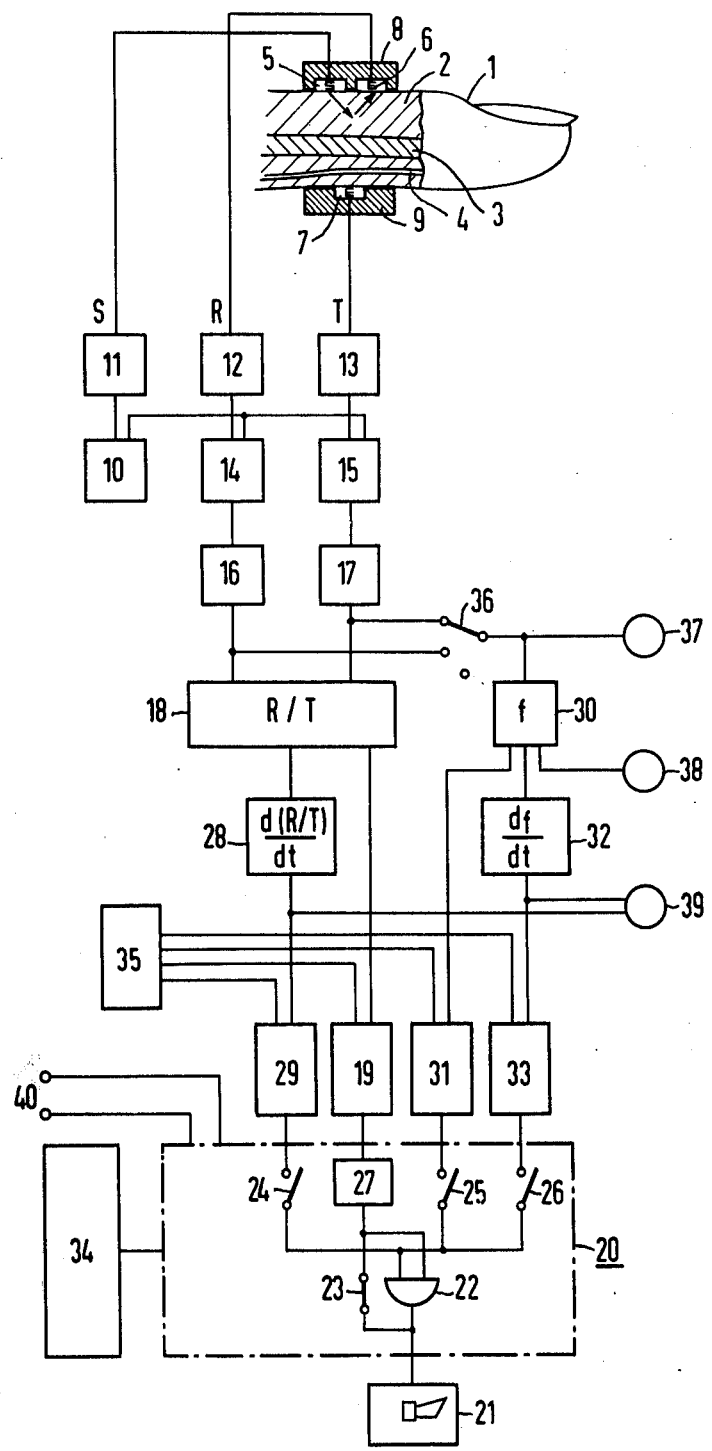

WARNING APPARATUS FOR INDICATING A THREAT OF IMPENDING SHOCK

FIELD OF THE INVENTION

The present invention relates to a warning apparatus for indicating the impending threat of shock, which includes a photoelectric pulse pickup or receiver adapted to be applied onto the skin of a patient.

The critical change in the condition of a patient which is designated by the concept "shock" may have different underlying causes. However, a few points of commonality may be determined in the various types of shock.

Thus, the central system forms herein an insufficient supply of oxygen to the tissues, which is frequently connected with a reduction in the flow of blood and rate of heart beat. Characteristic appearances in conditions of shock are changes in the blood pressure, the temperature, color and moisture of the skin, as well as in the cross-section and pulsations of peripheral tissues.

DISCUSSION OF THE PRIOR ART

A warning apparatus of the above-mentioned type is already known wherein, in addition to a photoelectric pulse pickup which selectively operates in either only reflective or transmissive mode, there is also included a rheographic skin resistance pickup or receiver which generates a signal in conformance with the skin resistance. This signal provides a criteria for the skin moisture of the probed person. At concurrent strong skin moisture and blood flow disturbances (bubbles) obtained from the pulse pickup, a signal is generated which, for example, by means of an alarm device, indicates the threatening shock.

A disadvantage in the known warning apparatus lies in that, for the detection of an impending threat of shock, there must be utilized two measured value receivers which are predicated on different measuring modes, together with associated correspondingly distinct signal processing installations having relatively complex technical requirements. Of greater advantage would be a warning apparatus which operates pursuant to a single measuring mode or procedure, preferably, an optical procedure.

SUMMARY OF THE INVENTION

Accordingly, it is an object of the present invention to provide a novel and inventive warning apparatus of the above-mentioned type which avoids the disadvantages encountered in the prior art.

The foregoing object is inventively attained in that the pulse pickup or receiver is a combined reflective and transmissive receiver, and the pulse pickup has a signal comparison arrangement associated therewith which compares the signal obtained from a reflective and transmissive measurement with predetermined signal threshold or boundary values, and which will generate an output signal for initiation of an alarm when the output signal of the pulse pickup exceeds the boundary value imparted thereto.

The invention is based on the recognition that photoelectric pulse pickups, dependent upon whether they operate in reflective or transmissive operation, have different signal entry ranges. In the application of pulse pickups onto a finger, for example, it is a fact that the reflected light is overwhelmingly modulated in the capillary blood flow tissues, whereas the transmitted light will, above all, represent the pulsations of the palmar finger arteries (A. digitales palmares) propiae). Whereas these signal entry ranges will, in the shock-free condition of the patient, deliver reflective and, respectively, transmissive signals of predetermined amplitude, at threatening shock there is produced a change in amplitude which occurs at different intensities for the two signal types. The differently strong amplitude variations may be detected by means of suitable threshold indicators, and be indicated as impending threat of shock, for example, by means of activation of an acoustic alarm. The apparatus according to the invention omits the technically relatively complex rheographic skin moisture measuring procedure and limits itself to merely two optical measurements, and wherein the signals which produced by the current measurement are processed by means of one and the same processing apparatus. Thereby, as desired, there is produced a warning apparatus which for the lowest possible technical requirements, provides optimum shock detection and indicating conditions.

In a particularly advantageous further construction of the invention, based on the circuit arrangement thereof, the comparator arrangement provides for a proportionality formulator which forms the proportionality signal R/T from the reflection signal R, as well as from the transmission signal T, and which has a boundary value indicator connected thereto which generates an output signal when the proportionality signal R/T exceeds or drops below a preset limit or boundary value. The proportionality signal R/T thus, in particular, eliminates time-dependent amplitude oscillations of the pulse curves caused by the patient himself, and thereby provides a particularly sharp shock criteria.

BRIEF DESCRIPTION OF THE DRAWING

Further advantages and details of the invention may now be ascertained from the following description of an exemplary embodiment of the invention, taken in conjunction with the single FIGURE of the accompanying drawing which shows a schematically illustrated warning apparatus.

DETAILED DESCRIPTION

In FIG. 1, designated by reference numeral 1, there is illustrated in part section the finger of a shock-endangered patient. The reference numeral 2 hereby applies to capillary blood conveying finger tissue, the reference numeral 3 relates to the finger bone, and the reference numeral 4 to a palmar finger artery. Located on the upper side of the finger is a light transmitter 5 proximate a first light receiver 6 for the light which is reflected from the finger, and correspondingly located on the lower side of the finger is a second light receiver 7 for the light which is transmitted through the finger. The plastic material carrier 8 for the transmitter 5 and the first light receiver 6, on the one hand, as well as carrier 9 for the second light receiver 7, on the other hand, may preferably be constructed as the arms or clamps of a hinge, or of a clamping arm receiver or pickup. The light transmitter 5 may be a normal glow lamp or lightbulb which projects light impulses into the finger 1 in the beat of a pulse transmitter 10 through an activating stage 11. However, there may just as well there be also employed luminescent diodes, or the like, as the light transmitter. The light receivers 6 and 7 are preferably photodiodes which produce electrical signals in conformance with the intensity of the presently received light.

The reflective signals R which are received from the receiver 6, after filtering and amplification in a frequency filter and amplifier element 12, are transmitted to a demodulator 14 which demodulates the signals in beat with the pulse transmitter 11 for the light transmitter. The corresponding procedure is also effected in the frequency filter and amplifier element 13 having the thereto connected demodulator 15 with respect to the transmission signals T received at the light receiver 10.

The thus demodulated signals, after further frequency filtering and amplification in the components 16 and 17, are then transmitted to a proportionality former 18 (divider stage) which forms the proportionality signal R/T. This proportionality signal R/T is then finally transmitted into a boundary value indicator 19, the latter of which generates an output signal when the proportionality signal in a situation of shock exceeds the amplitude of a preset boundary or limit value. The output signal of the threshold or boundary value indicator 19 is, in turn, transmitted to a logic circuit 20 having an alarm initiator connected thereto, for example, a loudspeaker stage 21.

The logic circuit 20, for example, incorporates an AND- element 22 in addition to control switches 23 through 26. For a closed switch 23, as well as open switches 24 through 26, the output signal of the boundary value indicator 19 for the proportionality signal R/T is transmitted through a delay element 27 directly to the alarm initiator 21. The delay element 27 hereby activates the alarm initiator 21 for producing an alarm only when the output signal of the boundary value indicator 19 is present for a predetermined time period, for example, 5 seconds. Erroneous indications of the presence of shock are thereby avoided. The delay element 27, for example, may be constructed as a free-running integrator, for example, an RC-stage, which increases in voltage with the incidence of a boundary or limit value output signal and reaches a voltage level after the predetermined delay period for initiation of the alarm, and in contrast therewith again set at zero by the previously reset boundary value indicator 19.

The switches 24 through 26, at an open switch 23, permit the selective connection to the AND-element 22 of further boundary value branched off from the reflective and transmissive signals R, respectively T, together with the proportionality signal R/T. Such boundary values, for example, are the timewise changes $$\frac{d(R/T)}{dt}$$

of the proportionality signal R/T obtained by means of a differentiating element 28 and thereto connected boundary value indicator 29, possibly the limit value of the pulse frequency $f$ obtained by means of pulse frequency measuring gauge 30 besides a limiting value indicator 31, or the limit value of the timewise change $df/dt$ of the pulse frequency $f$ detected by means of a differentiating element 32 in addition to boundary value indicator 33. Consequently, the alarm is initiated at the alarm initiator 21 always only when, in addition to the boundary value the proportionality signal R/T there is also produced a further boundary value the proportionality signal R/T, there is also produced a further boundary value signal of the signals $$\frac{d(R/T)}{dt},$$

$f$ or $df/dt$. Since the magnitudes $$\frac{d(R/T)}{dt}$$

(in particular, very rapid reductions in the amplitudes of the proportionality signals), pulse frequency $f$ (in particular high values), as well as $df/dt$ (in particular a rapid increase of pulse frequency), represent further threshold criteria for a threatening shock, then their AND-combination, together with the proportionality signal R/T, provides a particularly sharp confinement of the shock diagnosis.

The selection of the control switches 23 through 26 is carried out by means of a selector unit 34 for predetermined shock types. For effecting the setting of desired boundary values at the boundary value indicators 19, 29, 31 and 33, there is provided a boundary value input element 35. A switch 36 facilitates the selective connection of the pulse frequency measuring gauge 30 to the demodulated and filtered R or T signals, or the complete switching off of the two signals. The indicator apparatus 37, 38, 39 serve for indication of the R and T pulse curve, the pulse frequency $f$, or respectively, for indication of the change tendency of the proportionality signal R/T or, respectively, of the pulse frequency $f$.

The logic circuit 20, pursuant to the FIGURE of the drawing, facilitates the interconnection, in particular, of always two boundary value magnitudes. At a suitable construction, for example, with the use of further AND-elements, or an AND-element having more than two logic inputs, there may also be selectively combined more than only two of those values with each other, and may be incorporated into the shock indication an additional criteria for the threat of impending shock. Correspondingly, there may also be included further physiological values, for example, EKG, blood pressure, breathing frequency or the like, for instance through the additional inputs 40 of the logic circuit in the logic unit.

While there has been shown what is considered to be the preferred embodiment of the invention, it will be obvious that modifications may be made which come within the scope of the disclosure of the specification.

What is claimed is:

1. In a warning apparatus for indicating the threat of impending shock in a patient, including photoelectric pulse pickup means adapted to be applied to the skin of said patient and comprising at least one light transmitter and at least two light receivers, said light transmitter comprising substantially a light source, said light receivers converting incident light into corresponding electrical signals, said receivers comprising combined reflection and transmission receivers; signal comparison means having at least one threshold discriminator set to predetermined critical threshold values corresponding to upper and lower boundary values and being operatively connected to said pulse pickup means for comparing simultaneously signals obtained from a reflection and transmission measurement with said boundary values and to generate an output signal; and alarm means responsive to said output signal for initiating an alarm when the signals compared by said comparison means with said boundary values exceed or fall below said boundary values, said signals from said pickup means comprising simultaneous transmissive and reflective signals dependent on the physiological characteristics of a patient related to impending shock conditions.

2. A warning apparatus as claimed in claim 1, said signal comparison means comprising a delay element for initiation of the alarm, said delay element retarding initiation of said alarm for a predetermined time period during which the output signals of said pulse pickup means exceed or fall below the boundary values associated therewith.

3. A warning apparatus as claimed in claim 2, said predetermined time period being of a duration of about 5 seconds.

4. A warning apparatus as claimed in claim 1, comprising means for obtaining the speed of amplitude changes of the reflective and transmissive signals being operatively connected to said signal comparison means so as to generate an output signal upon exceeding predetermined speed limit values; an AND-element for said output signal and for the reflective and transmissive signals of said pulse pickup means, said AND-element generating a signal for initiating an alarm upon the output signal and the reflective and transmissive signals exceeding or falling below the boundary values associated therewith.

5. A warning apparatus as claimed in claim 1, comprising pulse frequency measuring means for measuring the blood pulse frequency from said reflective and transmissive signals being connected with said signal comparison means; and an AND-element being connected to said pulse frequency measuring means for initiating an alarm signal upon the pulse frequency, the differentiated pulse frequency after differentiation thereof, and the amplitudes of the reflective and transmissive signals exceeding or falling below the boundary values associated therewith.

6. A warning apparatus as claimed in claim 1, said pulse pickup means comprising a light transmitter and a first light receiver for reflected light adjacent thereto; and a second light receiver for transmitted light located opposite said light transmitter.

7. A warning apparatus as claimed in claim 6, said pulse pickup means comprising hinged clamping arms means, said light transmitter and said first light receiver being located on one arm and said second light receiver being located on a second arm of said hinged clamping arm means.

8. In a warning apparatus for indicating the threat of impending shock in a patient, including photoelectric pulse pickup means adapted to be applied to the skin of said patient and comprising at least one light transmitter and at least two light receivers, said light transmitter comprising substantially a light source, said light receivers converting incident light with corresponding electrical signals, and receivers comprising combined reflection and transmission receivers; signal comparison means having at least one threshold discriminator set to predetermined critical threshold values corresponding to upper and lower boundary values and being operatively connected to said pulse pickup means for comparing signals obtained from a reflection and transmission measurement with said boundary values and to generate an output signal; and alarm means responsive to said output signal for initiating an alarm when the signals compared by said comparison means with said boundary values exceed or fall below said boundary values, said signal comparison means comprising a proportionality former for producing a proportionality signal from said reflective signal and said transmissive signal; and a boundary value indicator being connected to said proportionality former and generating an output signal upon said proportionality signal exceeding or falling below a predetermined boundary value.

* * * * *